United States Patent [19]

Abbott et al.

[11] 4,247,703

[45] Jan. 27, 1981

[54] MICROBIOLOGICAL MODIFICATION OF ANTIBIOTIC A23187 ESTERS

[75] Inventors: Bernard J. Abbott, Greenwood; David S. Fukuda, Brownsburg, both of Ind.

[73] Assignee: Eli Lilly and Company, Indianapolis, Ind.

[21] Appl. No.: 971,616

[22] Filed: Dec. 20, 1978

[51] Int. Cl.$^3$ .................................... C07D 493/10
[52] U.S. Cl. .................................. 548/216; 435/119; 435/893
[58] Field of Search .................... 260/307 D; 548/216

[56] References Cited

U.S. PATENT DOCUMENTS 3,923,823  12/1975  Gale et al. ..................... 260/307 D
3,960,667  6/1976   Gale et al. ..................... 260/307 D

OTHER PUBLICATIONS

Kondorosi, Chem. Abs. 88, 16, 6181c, (1977).

*Primary Examiner*—Mark L. Berch
*Attorney, Agent, or Firm*—Nancy J. Harrison; Arthur R. Whale

[57] ABSTRACT

Cultivation of *Streptomyces chartreusis* NRRL 11407 in the presence of antibiotic A23187 methyl ester produces 16-hydroxy A23187 methyl ester, 16-hydroxy-N-demethyl A23187 methyl ester, and N-demethyl A23187 methyl ester. Hydrolysis of the products affords the corresponding free acids which form dimeric complexes with divalent cations.

2 Claims, No Drawings

MICROBIOLOGICAL MODIFICATION OF ANTIBIOTIC A23187 ESTERS

Antibiotic A23187 is an ionophoric compound that forms dimeric complexes with divalent cations, such as $Mn^{++}$ and $Ca^{++}$. The structural formula of antibiotic A23187 is depicted below in Formula I.

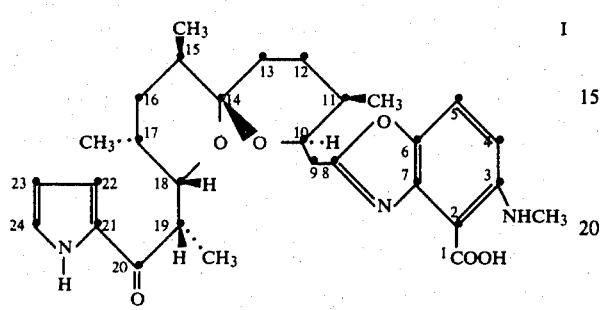

The numbering system employed for A23187 is that proposed by M. Chaney et al. *J. Antibiot.*, 29, 424 (1976). A23187 is one of the few naturally occurring compounds capable of transporting divalent cations across biological membranes. [See P. Reed et al., *J. Biol Chem.*, 247, 6970 (1972)]. Ion transport by A23187 is mediated by a dimeric form of the molecule that complexes the cation [See M. Chaney et al., *J. Am. Chem. Soc.*, 96, 1932 (1974); P. Reed et al., supra; and D. Pfeiffer et al. *Biochemistry*, 13, 4007 (1974)]. The relative stabilities of the complexes formed with cations are $Mn^{++} > > Ca^{++} \simeq Mg^{++} > > Sr^{++} > Ba^{++}$ [See D. Pfeiffer et al. supra].

A23187 elicits a wide range of pharmacological responses, e.g. platelet aggregation [See P. Worner et al., *Thrombosis Res.*, 6, 295 (1975)], insulin release, [See C. Wollheim et al., *J. Biol. Chem.*, 250, 1354 (1975)], histamine release [J. Foreman et al. *Nature*, 245, 249 (1973)], increased cardiac contractility [See D. Holland et al., *Proc. Soc. Exptl. Biol. Med.*, 148; 1141 (1975)], arrest of sperm motility [See D. Babcock et al., *J. Biol. Chem.*, 251, 3881 (1976)], and release of slow reacting substance [M. Bach, *J. Immuol.*, 113, 2040 (1974)].

Antibiotic A23187 is prepared by culturing the microorganism *Streptomyces chartreusis*, NRRL 3882, as described by Gale et al., U.S. Pat. Nos. 3,923,823 and 3,960,667. The present invention relates to novel derivatives of A23187 produced by the biotransformation of an A23187 (lower) alkyl ester and to the products formed by the hydrolysis of such derivatives. Also contemplated are the processes for carrying out the aforesaid biotransformations.

In its first aspect, the invention sought to be patented comprises alkyl ester derivatives of A23187 which have the formulae:

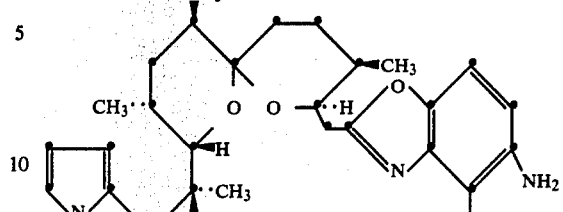

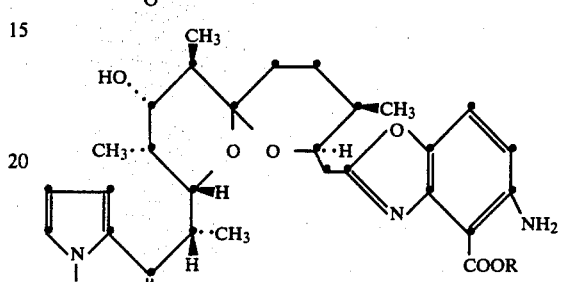

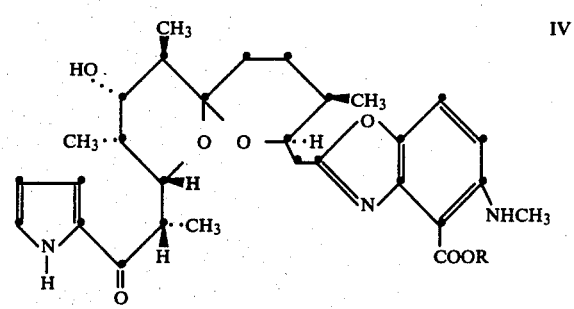

wherein R is methyl, ethyl, n-propyl, isopropyl, n-butyl, i-butyl, or t-butyl.

In the above formulae (and those appearing hereinafter), the dotted lines indicate that the bonded group is partially located below the plane of the ring to which it is attached. The spikes indicate that the attached group is positioned above the plane of the ring.

In its second aspect, the invention contemplates the hydrolysis products of the compounds of formula II, III, or IV, which products have the formulae:

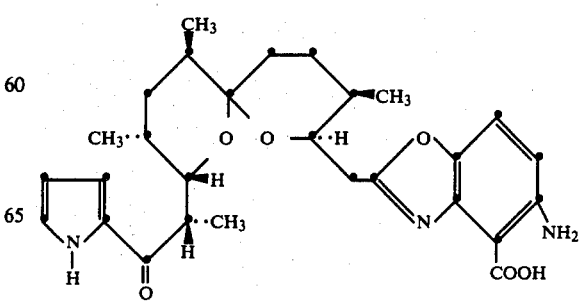

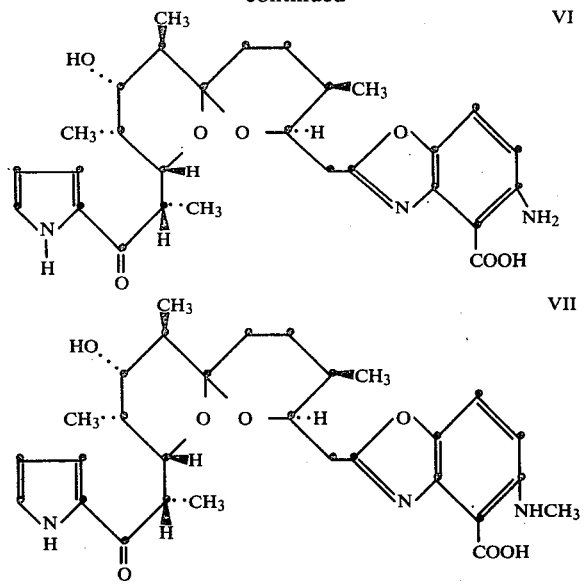

| Compound | Ion Preference |
|---|---|
| 16-Hydroxy-N-demethyl A23187 | $Mn^{++} >> Mg^{++} > Ca^{++} > Sr^{++} > Ba^{++}$ |
| 16-Hydroxy A23187 | $Mn > Ca^{++} > Mg^{++} > Sr^{++} > Ba^{++}$ |
| A23187 | $Mn^{++} >> Ca^{++} \simeq Mg^{++} >> Sr^{++} > Ba^{++}$ | or a sodium, potassium, or lithium salt thereof; or a dimeric complex thereof with a divalent cation selected from the group consisting of berylium, magnesium, calcium, strontium, barium, manganese, cadmium, iron, zinc, lead, and mercury.

The monovalent cation salts of the compounds of Formula V, VI, and VII are prepared by conventional means such as by treating the acid with an appropriate base containing the desired monovalent cation. The divalent complexes of the aforesaid compounds are represented by the formula $A_2M$ wherein A represents a compound of Formula V, VI, or VII and M is a divalent cation as hereinabove defined. The complexes are prepared by conventional means such as by treating an alkaline metal salt of the compound in water with the desired divalent cation. The complexes may also be made by adding the divalent cation to a water solution of the compound at neutral pH. Suitable sources of the divalent and monavalent cations will be apparent to those skilled in the art.

For convenience herein, the compounds of the invention will be identified as A23187 derivatives, as follows:
Compound II: N-demethyl A23187 (lower) alkyl ester
Compound III: 16-hydroxy-N-demethyl-A23187 (lower) alkyl ester
Compound IV: 16-hydroxy A23187 (lower) alkyl ester
Compound V: N-demethyl A23187
Compound VI: 16-hydroxy-N-demethyl-A23187
Compound VII: 16-hydroxy A23187.

As used herein and in the claims "lower alkyl" means methyl, ethyl, propyl, n-propyl, n-butyl, i-butyl, or t-butyl. The methyl group is preferred.

The esters of Formula II, III, and IV are intermediates for the preparation of the free carboxylic acid compounds of Formula V, VI, and VII, which are ionophoric and possess the ability to form complexes with certain divalent cations. The ion specificities of Compounds VI, and VII, and A23187, as determined by fluorescence quenching measurements, according to the procedure of D. Pfeiffer et al., *Biochemistry*, 13, 4007 (1971), are as follows:

Because of their preferential binding properties the compounds of Formula V, VI, and VII are useful in applications wherein the selective removal of a particular cation is desired.

When tested according to the procedure of D. Wong et al. *Arch. Biochem. and Biophys.* 156, 578 (1973), the compounds of Formula VI or VII have been found to inhibit $Ca^{++}$ dependent ATPase and to activate oxygen uptake in liver mitochondria, the activity being about 1/5 to about 1/10 that of A23187. Thus it is indicated that the compounds act in the mitochondria to transport divalent cations, such as $Ca^{++}$. Said compounds are also useful in the study of cation binding and transport selectivity patterns for divalent cations of biochemical importance (e.g. $Ca^{++}$). Such studies are important, for example, in research concerning (a) the mechanisms of regulating intracellular ionic distributions and concentrations and (b) the involvement of the intracellular ionic environment in the regulation of cellular functions.

The (lower) alkyl esters of Formula II, III, or IV are unable to form a salt or dimeric complex with a divalent cation, since the carboxyl group must be free for salt or complex formation to occur. Alkaline hydrolysis of a (lower) alkyl ester, however, affords the corresponding free acid (V, VI, or VII).

The esters of Formula II, III, or IV are prepared by the biotransformation of a (lower) alkyl ester of antibiotic A23187. The preferred microorganism for the biotransformation is a strain of *Streptomyces chartreusis*, Calhoun and Johnson. This strain is different from the strain of *Streptomyces chartreusis* NRRL 3882 used for the preparation of antibiotic A23187. The strain employed for the biotransformation of antibiotic A23187 has been deposited with the permanent culture collection of the Northern Utilization Research and Development Division, Agricultural Research Service, U.S. Department of Agriculture, Peoria, Ill. Its accession number in this collection is NRRL 11407. The strain was isolated from a soil sample collected in Venezuela by suspending portions of the sample in sterile deionized water and streaking the suspension on nutrient agar in petri dishes. After incubation at 25°-35° C., until growth was attained, colonies of the organism were transferred to agar slants with a sterile platinum loop. The agar slants were then incubated to provide a suitable inoculum for the culture of the organism used for the biotransformation.

The biotransformation of a A23187 lower alkyl ester to obtain a compound of Formula II, III, or IV, is accomplished by cultivating *Streptomyces chartreusis* NRRL 11407 in a culture medium containing assimilable sources of carbon, nitrogen, and inorganic salts under submerged aerobic conditions; adding the A23187 lower alkyl ester to the culture medium; and incubating the culture medium until substantial amounts of the desired transformation products are formed. Under these conditions, a mixture of the following lower alkyl esters is produced: 16-hydroxy A23187 (Formula IV); N-demethyl A23187 (Formula II); and 16-hydroxy-N-demethyl A23187 (Formula III). Starting from A23187 methyl ester the transformation products are isolated in a yield of from 4-6% (by weight) from the substrate. The mixture of transformation products is recovered from the culture medium by methods conventional in the fermentation art, e.g. by solvent extraction. The transformation products are separated, isolated, and purified by chromatography.

After the finding that N-demethyl A-23187 methyl ester is a biotransformation product of A23187 methyl ester, it was discovered that N-demethyl A23187 is formed as a minor factor during the preparation of antibiotic A-23187 but the cultivation of *Streptomyces chartreusis* NRRL 3882. However, control experiments have demonstrated that N-demethyl A-23187 methyl ester is produced from A23187 methyl ester by *Streptomyces chartreusis* NRRL 11407. The yield of the N-demethyl product with NRRL 11407 is considerably higher than can be accounted for by the presence of N-demethyl A-23187 methyl ester in the starting substrate.

The structures of the transformation products of Formula II, III, and IV were determined by high resolution mass spectrometry and proton magnetic resonance spectrometry.

It should be recognized that A23187 as the free carboxylic acid cannot be used as a substrate for cultivation with *Streptomyces chartreusis* NRRL 11407. An ester derivative of A23187 is essential for utilization by the organism. Thus, in order to obtain transformation products of A23187 having ionophoric properties the preparation must include formation of the alkyl ester of A-23187, incubation of the ester with *Streptomyces chartreusis* NRRL 11407, and hydrolysis of the ester.

It should also be noted that a number of organisms other than *Streptomyces chartreusis* NRRL 11407 may be employed for the transformation of an A23187 ester. However, *Streptomyces chartreusis* NRRL 11407 is preferred because it produces the best yield of transformation products. As is the case with other organisms, the characteristics of *Streptomyces chartreusis* NRRL 11407 are subject to variation. For example, artificial variants and mutants of the NRRL 11407 strain may be obtained by treatment with various known mutagens, such as ultraviolet rays, X-rays, high-frequency rays, radioactive rays, and chemicals. All natural and artificial variants and mutants of *Streptomyces chartreusis* NRRL 11407 which are capable of producing the transformation products may be used in this invention.

Characterization of *Streptomyces chartreusis* NRRL 11407

The NRRL 11407 culture employed for biotransformation of A23187 has been classified as a strain of *Streptomyces chartreusis*, Calhoun and Johnson, based upon a comparison with the published description. Culture NRRL 11407 differs principally from the published description of *Streptomyces chartreusis* in the tolerence for sodium chloride.

The methods employed for the characterization are those recommended for the *International Streptomyces Project* for the characterization of streptomyces species [E. Shirling and D. Gottlieb, *Intern. Bull, of Systematic Bacteriol.*, 16, 313 (1966)]. Certain supplementary tests have also been employed. Color names are assigned according to the Inter-Society Color Council-National Bureau of Standard (ISCC-NBS) method [K. Kelly and B. Judd, *The ISCC-NBS Methods of Designating Color and a Dictionary of Color Names* U.S. Department of Commerce, Circ. 553, Washington, D.C., 1955.] Figures in parenthesis refer to the Tresner and Backus color series [H. Tresner and L. Backus, *Appl. Microb.*, 11, 335 (1956)]. Color tab designations are *underlined*. The Marz and Paul color blanks are entered in brackets. [A. Marz and M. Paul, *Dictionary of Color*, McGraw Hill Book Co., Inc., N.Y. 1950.]

Cultures were grown at 30° C. unless otherwise noted. The cell wall sugars were determined using a modification of the procedure of M. Lechevalier, "Chemical Methods as Criteria for the Separation of Actinomycetes into Genera", Workshop sponsored by the Subcommittee on Actinomycetes of the American Society of Microbiology, Dr. Thomas G. Pridham, Convenor, held at the Institute of Microbiology, Rutgers University, New Brunswick, N.J., 1971. The isomer of diaminopimelic acid was determined using the method of B. Becker *Appl. Microbiol.*, 11, 421 (1964). Results of the taxonomic studies are summarized below:

Morphology

Spiralled sporophores are produced with spirals of 4-6 turns frequently observed. The spores per chain are generally 10-50; some chains were observed with more than 50 spores per chain. The spores are oval to spherical and measure on the average 1.30 $\mu$m × 1.43 $\mu$m with a range of 1.30 $\mu$m × 1.30 $\mu$m to 1.95 $\mu$m. The spores are spiny as determined by electron micrographs.

| Cultural Characteristics of NRRL 11407 | |
|---|---|
| Medium | Characteristics |
| ISP medium #2 (yeast-malt extract agar) | Abundant growth, reverse light brown [12I8]. Aerial mycelium abundant. Blue (B) 19fe pale blue; no soluble pigment. |
| ISP medium #3 (Oatmeal agar) | Abundant growth, reverse light grayish olive [14B2]; aerial mycelium abundant, Blue (B) 19fe pale blue; none or slight brown soluble pigment. |
| ISP medium #4 (Inorganic salts-starch agar) | Abundant growth, reverse light grayish yellowish brown [13D2]; aerial mycelium, abundant, Gray (GY) g medium gray; no soluble pigment. |
| ISP medium #5 (Glycerol asparagine agar) | Abundant growth, reverse dark grayish olive [13K3]; aerial mycelium, abundant; Blue (B) 19fe pale blue; slight brown soluble pigment. |
| Bennett's modified agar | Abundant growth, reverse medium yellow brown [14I8]; aerial mycelium, abundant, Blue (B) 19fe pale blue; no soluble pigment. |
| Calcium malate agar | Fair to good growth, reverse yellowish gray [11A1]; aerial mycelium. Fair to good, Blue (B) 19fe pale blue; none or a slight brown soluble pigment. |
| Emerson's agar | Growth good to abundant, reverse medium brown [14I10] medium brown; aerial mycelium, good to abundant; Gray (GY) d light gray to White (W) b white; no soluble pigment. |
| Czapek's solution agar | Growth abundant, reverse grayish yellow [12D3]; aerial mycelium, abundant, White (W) b white; slight brown soluble pigment. |
| Tryptone yeast extract agar | Growth abundant, reverse grayish yellowish brown [14C6]; aerial mycelium fair to good, Gray (GY) d light gray; no soluble pigment. |
| Nutrient agar | Growth fair to good, reverse |

Cultural Characteristics of NRRL 11407 -continued

| Medium | Characteristics |
|---|---|
| | medium yellowish brown [14F6]; aerial mycelium scant, White (W) b white to Gray (GY) d light gray; no soluble pigment. |
| Glucose asparagine agar | Growth abundant, reverse light yellow brown [13C6]; aerial mycelium abundant, Blue (B) 19fe pale blue. No soluble pigment. |
| Glycerol-glycine agar | Abundant growth, reverse pale yellow [13F2]; aerial mycelium, abundant, White (W) 13ba purplish white to Blue (B) 19dc pale blue; no soluble pigment. |
| Tomato paste oatmeal agar | Abundant growth, reverse grayish yellowish brown [15E7]; aerial mycelium, abundant, Blue (B) 19fe pale blue; no soluble pigment. |
| Tyrosine agar | Abundant growth, reverse dark grayish olive [8C10]; aerial mycelium, good to abundant, Gray (GY) 2ge light olive brown; brown soluble pigment. |

Carbon Utilization

| Substrate: Carbon sources added to Pridham and Gottlieb's basal medium. | Reaction of NRRL 11407 at 16 days |
|---|---|
| Adonitol | ++ |
| D(−)Arabinose | + |
| L-Arabinose* | + |
| D(+)Arabitol | ++ |
| L-Arabitol | − |
| D(+)Cellulose | ++ |
| α-Cellulose | − |
| Dulcitol | − |
| i-Erythritol | − |
| Esculin | ± |
| D(−)Fructose* | + |
| α-D(+)Fructose | − |
| α-L(−)Fructose | ++ |
| D(+)Galactose | ++ |
| D(+)Glucosamine | + |
| D(−)Glucose* | ++ |
| α-ME-D-Glucoside | + |
| β-Me-D-Glucoside | Not Tested |
| i-Inositol* | ++ |
| Inulin | ++ |
| Lactose | ++ |
| D(+)Maltose | ++ |
| D(−)Mannitol* | ++ |
| D(+)Mannose | ++ |
| α-Me-D-Mannoside | ± |
| Melibiose | ++ |
| D(+)Melezitose H$_2$O | − |
| Palatinose | ++ |
| D(+)Raffinose* | ++ |
| L-Rhamnose* | ++ |
| D(−)Ribose | ++ |
| Salicin | Not tested |
| D(−)Sorbitol | ++ |
| L(−)Sorbose | − |
| Soluble Starch | ++ |
| Sucrose* | ++ |
| D(−)Tagatose | − |
| D(+)Trehalose | ++ |
| D(+)Turanose | + |
| D(+)Xylose* | + |
| α-Me-D-Xyloside | − |
| β-Me-D-Xyloside | + |
| Xylitol | − |

Key:
++ = Strong Positive Utilization
+ = Positive Utilization
± = Utilization doubtful
− = Negative Utilization
*Carbon sources of the International *Streptomyces* Project (6)

Physiological Properties of Culture NRRL 11407

| Test | Reaction of Culture NRRL 11407 |
|---|---|
| Melanoid Pigment Production on: | |
| 1. Tryptone yeast extract broth. | Melanoid-like pigment produced. |
| 2. Peptone yeast extract iron slants | Melanoid-like pigment produced. |
| 3. Tyrosine agar slants | Slight black pigment produced at base of agar slope. |
| Nitrate Reduction | Red color with reagents. (Positive) |
| Gelatin Liquifaction | No liquifaction by 14 days; nutrient gelatin tubes darkened. |
| Potato Plug | Excellent growth by 7 days. Brown vegetative; white to greenish blue aerial mycelium. |
| Carrot Plug | Abundant growth by 14 days. Brown vegetative; blue aerial mycelium. |
| Starch Hydrolysis Use ISP medium #4 (Inorganic salts - starch agar) | Starch hydrolyzed. |
| Temperature Requirements use ISP medium #2. (Yeast extract - malt extract agar) | Optimum temperature 25° C.–37° C. No growth at <25° C. or >37° C. |
| Skim Milk | Milk peptonized. |
| NaCl Tolerance: | |
| NaCl was added to ISP medium #2 Yeast-malt extract agar at levels of 1%, 2%, 3%, 4%, 6%, 8%, 10%, 12% and 14%. Plates | Growth and sporulation ≧4% but <6%. |

| Physiological Properties of Culture NRRL 11407 | | |
| --- | --- | --- |
| Test | Reaction of Culture NRRL 11407 | |
| were examined after 12 days incubation. | | |
| Reaction to changes in pH ISP medium #2, yeast-malt extract agar was used. pH adjustments were made after autoclaving for sterilization. The pH levels used were pH 4.5 to pH 11.0 increments of 0.5 pH units. | At pH levels pH 5.0 to 8.5 pH 9.0 to 11.5 | <5.0 no growth. good growth; good blue aerial mycelium still good growth and aerial mycelium. but blue aerial progressively lost and replaced with white aerial by pH 11.5 |

Cell Wall Studies

1. Diaminopimelic acid (DAP): LL Isomer
2. Whole Cell Sugars detected: Glucose, Ribose The similarities and differences of culture NRRL 11407 and the published description of *Streptomyces chartreusis* Calhoun and Jackson, 1956 are outlined below.

| | Culture Similarities & Differences | |
| --- | --- | --- |
| Characteristic, Reaction etc. | NRRL 11407 | *Streptomyces chartreusis* Calhoun and Jackson, 1956 |
| Morphology | Spiralled | Spiralled |
| Spore ornamentation | Spiny | Spiny |
| Melanoid pigment production | Positive | Positive |
| Aerial mycelium | Principally blue | Blue |
| Spore shape and size | oval to spherical 1.3 μm × 1.43 μm | Spherical to oval 1.0 μm to 1.5 μm per diameter |
| Gelatin Liquifaction | None at 14 days | Slow |
| Skim milk | Peptonized | Peptonized |
| Carbon utilization | Identical on ISP series of carbon sources. | |
| | Culture Differences | |
| NaCl tolerance | 1% to 4% NaCl | ≧7% but <10% |

In addition to *Streptomyces chartreusis*, 3 cultures, *Streptomyces coerulescens*, *Streptomyces lanatus* and *Streptomyces viridochromogenes*, are also listed in the description [R. Buchanan et al. "Bergey's Manual of Determinative Bacteriology", The Williams and Wilkins Co., 8th Ed., 1974, p. 820] of the Spiralled, Blue Aerial, Spiny spored, melanoid pigment positive group. All organisms have essentially the same carbon utilization pattern. *Streptomyces coerulescens* differs from NRRL 11407 in the production of a yellow orange vegetative mycelium. The difference between *Streptomyces lanatus* and NRRL 11407 is the production of a reddish brown vegetative mycelium by the former. *Streptomyces viridochromogenes* differs from NRRL 11407 in the production of a green or black aerial color on some media.

*Streptomyces chartreusis* NRRL 3882, the microorganism that produces antibiotic A23187, differs from *Streptomyces chartreusis* NRRL 11407, the microorganism that modifies A23187 methyl ester, by the following characteristics: Culture NRRL 3882 was isolated in 1965 from a soil sample obtained from India. Culture NRRL 11407 was isolated in 1975 from a Venezuelan soil sample. Culture NRRL 11407 produces heavy aerial mycelia on Emerson agar and Czapek's solution agar, but culture NRRL 3882 does not produce aerial mycelia on these media. Culture NRRL 11407 produces a brown soluble pigment on tyrosine agar, and no soluble pigment is produced on ISP #4 medium. In contrast, culture NRRL 3882 does not produce a soluble pigment on tyrosine agar, but it produces a brown soluble pigment on ISP #4 medium. The temperature optima for growth of the two cultures also differ. Culture NRRL 11407 will grow at temperatures >40° C., but culture NRRL 3882 will not grow at temperature >37° C.

The medium employable to cultivate *Streptomyces chartreuses* NRRL 11407 can be any one of several media. However, for economy of production, maximum yield of antibiotic, and ease of isolation of the antibiotic, certain culture media containing relatively simple nutrient sources are preferred. Thus, for example, glucose and dextrin are preferred sources of carbohydrate, although fructose, sucrose, mannitol, starch and the like can also be employed. Preferred sources of nitrogen include corn steep solids, beef extract, casein, soybean meal and the like.

Nutrient inorganic salts to be incorporated in the culture media can include the customary salts capable of yielding sodium, potassium, iron, magnesium, ammonium, calcium, phosphate, chloride, sulfate and like ions. Additionally, sources of growth factors such as distillers' solubles and yeast extracts can be included with enhanced results.

As is necessary for the growth and development of other microorganisms, essential trace elements should also be included in the culture medium for growing the actinomycete employed in this invention. Such trace elements are commonly supplied as impurities incidental to the addition of other constituents to the media.

The initial pH of the culture medium can be varied widely. However, it has been found desirable that the initial pH of the medium be between about 6.0 and about 7.5. As has been observed with other actinomycetes, the pH of the medium gradually increases throughout the growth period of the organism and may attain a level from about 6.5 to about 8.0, the final pH being dependent at least in part on the initial pH of the medium, the buffers present in the medium, and the period of time the organism is permitted to grow.

Submerged, aerobic cultural conditions are the conditions of choice for the cultivation. For the production of relatively small amounts, shake flasks can be employed; but for the preparation of large amounts, submerged aerobic culture in sterile tanks is preferred. The medium in the sterile tank can be inoculated with a sporulated suspension; but because of the growth lag experienced when a sporulated suspension is used as the inoculum, the vegetative form of the culture is preferred. By thus avoiding the growth lag, more efficient use of the fermentation equipment is realized. Accordingly, it is desirable first to produce a vegetative inoculum of the organism by inoculating a relatively small quantity of culture medium with the spore form of the organism, and when a young, active vegetative inoculum has been obtained, to transfer the vegetative inoculum aseptically to the large tank. The medium in which the vegetative inoculum is produced can be either the same as or different from the medium utilized for the large scale production.

The organism grows best at temperatures in the range of about 26° C. to about 33° C. Optimal production appears to occur at temperatures of about 30° C.

As is customary in aerobic submerged culture processes, sterile air is blown through the culture medium. For efficient growth of the organism, the volume of air in the tank preferably is upwards of 0.1 volume of air per minute per volume of culture medium. Optimal growth is obtained when the volume of air used is at least one-half volume of air per minute per volume of culture broth.

In general, maximum growth occurs within about 2 to 5 days after inoculation of the culture medium when submerged aerobic culture or shake flask culture is employed.

About 2 to 5 days (preferably 3 days) after the start of the cultivation, the A23187 lower alkyl ester, preferably as an aqueous suspension, is added to the culture medium. A suspending agent, such as polyvinylpyrrolidone, can be employed, if desired. After addition of the substrate, the culture medium is incubated for an additional 2- to 5-day period, preferably 3 days.

The biotransformation products can be recovered from the mycelium by methods conventional in the fermentation art. Extraction techniques are preferred. For example, the culture medium can be extracted by a water-immiscible solvent (e.g. ethyl acetate) in which the desired products are soluble. If desired, the mycelium can be removed by filtration or centrifugation prior to extraction. The crude products, obtained after extraction and removal of solvent, can be separated by conventional techniques such as chromatography. A preferred technique employs reverse-phase high pressure liquid chromatography on a silica gel $C_{18}$ adsorbent. In this procedure, the crude product dissolved in methanol-water (65:35) is applied to the column. Elution with the same solvent removes the 16-hydroxy A23187 ester and 16-hydroxy-N-demethyl A23187 ester. Elution with methanol-water (90:10) removes the N-demethyl A23187 ester. The fractions can be monitored by means of a ultraviolet spectrophotometer by measuring absorption at 390 nm. Final purification can be achieved by re-chromatography, such as by preparative thin-layer chromatography using silica gel and development with tetrahydrofuran:cyclohexane:methanol (1:1:0.1).

The transformation products, prepared and isolated as above-described are converted to the free acids by alkaline hydrolysis with ethanolic potassium hydroxide followed by neutralization with acid.

The substrate A23187 lower alkyl esters may be prepared by conventional procedures from A23187. For example, the methyl ester can be prepared by treatment of A23187 with ethereal diazomethane.

The processes of the invention are illustrated by the following Examples:

EXAMPLE 1

Methylation of A23187

Ethereal diazomethane was prepared by adding 20 ml of a cold 40% KOH solution containing 7.0 g of N-nitrosomethylurea to 150 ml of diethylether in an ice bath. After the nitrosomethylurea reacted, the ether layer was decanted and dried with KOH. A23187 (1.5 g) was dissolved in cold 33% ethyl ether/67% methanol and then added to the chilled diazomethane solution. The mixture was allowed to react overnight at room temperature and then glacial acetic acid was added to destroy unreacted diazomethane. Ether and methanol were removed in vacuo. Water was then added and the mixture was extracted three times with chloroform. The extracts were combined, washed with water, dried over $Na_2SO_4$, and evaporated in vacuo to yield 1.3 g of A23187 methyl ester.

EXAMPLE 2

Biotransformation of A23107 methyl ester

Stock cultures of *Streptomyces chartreusis* NRRL 11407 were maintained on Bennett's agar slant medium. The slants were incubated for 72–96 hours at 25°–30° and then stored at 4°.

A culture medium having the following composition was prepared:

| | | |
|---|---|---|
| Glucose | 15.0 | g |
| Soybean meal | 15.0 | g |
| corn steep solids | 10.1 | g |
| tapioca dextrin | 20.0 | g |
| $CaCO_3$ | 2.0 | g |
| mineral mixture* | 2 | ml |
| tap water | 1 | liter |

*Prepared by dissolving 10 g KCl, 10 g $MgSO_4 \cdot 7H_2O$, 0.2 g $FeSO_4$; and 2 ml. 12N HCl in 100 ml. distilled water.

Two liters of the above medium were dispensed in 200 ml aliquots into 1.0 L. Erlenmeyer flasks. The flasks were closed with cotton plugs and autoclaved at 121° for 40 minutes. Each flask was inoculated with a loop transfer from an agar slant culture. After 96 hours of cultivation a suspension of A23187 methyl ester and polyvinylpyrrolidone (PVP) was added to each flask to achieve an 0.5 mg/ml final concentration of A23187 methyl ester. A PVP/substrate suspension was prepared by dissolving 1 part (by weight) A23187 methyl ester and 10 parts (by weight) PVP in chloroform. The chloroform was then removed in vacuo. The resultant dry powder was slurried in sterile water and then added to the cultures.

Transformation products were recovered from the cultures 96 hours after substrate addition by extraction with ethyl acetate. Each culture was extracted 3 times, and the extracts from all the flasks were combined, dried with $Na_2SO_4$, and evaporated to dryness in vacuo. The dry residue (1.3 g) was chromatographed on a reverse phase high performance liquid chromatography column (Quantum Industries, Fairfield, N.J.). The column was $1'' \times 12''$ stainless steel packed with (10–20μ particle size) LP-1 silica treated with octadecyltrichlorosilane. The column was operated at 300–750 psi with a Lapp pump (Intepace Corp., Leroy, N.Y.) to achieve a solvent flow rate of 20 ml/min. Effluent from the column was monitored with a Variscan Model 635LC Detector (Varian Assoc., Palo Alto, CA) at 390 nm. The sample was dissolved in 5.0 ml of a solvent mixture consisting of 65% methanol/35% $H_2O$ and applied to the column. Two transformation products, 16-hydroxy A23187 methyl ester and N-demethyl-16-hydroxy A23187 methyl ester, were eluted with 65% methanol/35% $H_2O$. Methanol:$H_2O$ (90:10) was used to elute N-demethyl A23187 methyl ester. Final purification of all products was achieved by preparative thin layer chromatography using silica gel G $F_{254}$ plates developed with a solvent mixture consisting of tetrahydrofuran:cyclohexane:methanol (1:1:0.1).

The mass spectrum of 16-hydroxy-N-demethyl A23187 methyl ester has a molecular ion $C_{29}H_{37}N_3O_7$, m/e 539; i.e., substrate plus oxygen less $CH_2$. Also present in the spectrum were fragment ions $C_{10}H_{13}NO$ m/e 163, and $C_{16}H_{18}N_2O_5$, m/e 318. The presence of these fragments indicated that the added oxygen was associated with carbon 15, 15', or 16 and that demethylation had occurred in the moiety giving rise to m/e 318. Although m/e 163 is of relatively low intensity, its assignment is supported by the presence of ions of the same composition in the spectra of A23187 and its methyl ester. Also, m/e 318 is the analog of the ion of the same composition which occurs in the mass spectrum of A23187. The H-1 NMR spectrum of this product lacks the usual methyl resonance near δ3.0 and shows small differences in the spectrum of the benzoxazole portion of the molecule, but is otherwise very similar to the spectrum of 16-hydroxy A23187 methyl ester.

The product assigned the 16-hydroxy A23187 methyl ester structure had a parent ion in its mass spectrum whose composition was one oxygen greater than substrate. Fragments at m/e 163 and 332 again indicated that the added oxygen was associated with carbons 15, 15', or 16. The H-1 NMR spectrum of the compound was essentially identical to that of the substrate except for the presence of a doublet or doublets at δ3.71. Through a series of decoupling experiments this resonance was shown to be due to a proton at C(16). This proton was coupled to H(17) by a coupling constant of 4.3 hz. The remaining coupling, by elimination due to H(15), was large (J=10.4 hz), showing that the structure and conformation of this portion of the molecule can be represented as follows:

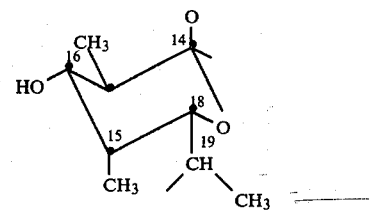

The molecular ion of N-demethyl A23187 methyl ester had a composition $CH_2$ less than the substrate and the fragmentation pattern was consistent with the loss of a $CH_2$ fragment from the benzoxazole portion of the molecule. The H-1 NMR spectrum of this product was essentially identical to that of the substrate except for the absence of the N-methyl resonance near δ3.

The chromatographic mobilities (TLC) and the molecular weight and empirical formulae (as determined from high resolution mass spectal data) of A23187 methyl ester and its biotransformation products are set forth in Table 1 below:

TABLE 1

Chromatographic Mobilities and High Resolution Mass Spectral Molecular Weights and Empirical Formulae of A23187 Methyl Ester and its Transformation Products

| Compound | $R_f$[1] | Molecular Weight Found | Molecular Weight Calculated | Empirical Formula[2] |
|---|---|---|---|---|
| A23187 Methyl Ester | 0.51 | | | $C_{30}H_{39}N_3O_6$ |
| 16-Hydroxy-N-demethyl A23187 Methyl Ester | 0.27 | 539.2645 | 539.2632 | $C_{29}H_{37}N_3O_7$ |
| 16-Hydroxy A23187 Methyl Ester | 0.37 | 553.2790 | 553.2788 | $C_{30}H_{39}N_3O_7$ |
| N-Demethyl A23187 Methyl Ester | 0.44 | 523.2685 | 523.2683 | $C_{29}H_{37}N_3O_6$ |

[1] Silica gel G $F_{254}$ thin layer plates, tetrahydrofuran:cyclohexane:methanol (1:1:0.1).
[2] Calculated from the high resolution mass spectrum.

EXAMPLE 3

Hydrolysis of Esterified Transformation Products

Methyl ester transformation products of A23187 were hydrolyzed to free acids with ethanolic KOH. The reaction was initiated by adding 0.3 ml of a 10% KOH solution to 5.0 ml of ethanol containing 5.0 mg of transformation product. The mixture was reacted at 60° C. for 3 hours. Water (12.0 ml) was then added and the pH of the solution was lowered to 4.5 with 0.1 N HCl. The ethanol was removed in vacuo and the remaining aqueous suspension was extracted three times with ethyl acetate to recover about 4.5 mg of acidic product. Thin layer chromatography and high performance liquid chromatographic analyses indicated that >95% of the methyl ester was hydrolyzed and little or no side products were produced.

The molecular weight and empirical formulae (as determined from high resolution mass spectral data) are set forth in Table II below:

TABLE 2

High Resolution Mass Spectral Data from A23187 and its Transformation Products

| Compound | Molecular Weight Found | Molecular Weight Calculated | Empirical Formula[1] |
|---|---|---|---|
| A23187 | | | |

TABLE 2-continued

High Resolution Mass Spectral Data from A23187 and its Transformation Products

| Compound | Molecular Weight | | Empirical Formula[1] |
|---|---|---|---|
| | Found | Calculated | |
| 16-Hydroxy-N-demethyl A23187 | 525.2466 | 525.2475 | $C_{28}H_{35}N_3O_7$ |
| 16-Hydroxy A23187 | 539.2629 | 539.2632 | $C_{29}H_{37}N_3O_7$ |
| N-Demethyl A23187 | 509.2529 | 509.2526 | $C_{28}H_{35}N_3O_6$ |

[1]Calculated from the high resolution mass spectrum.

What is claimed is:

1. A compound of the formula:

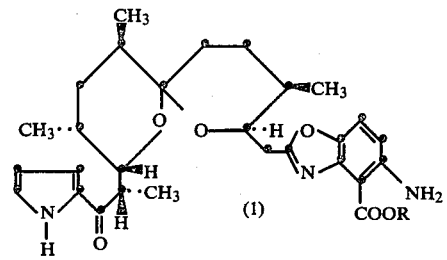

(1)

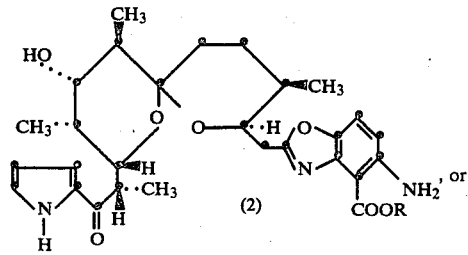

(2)

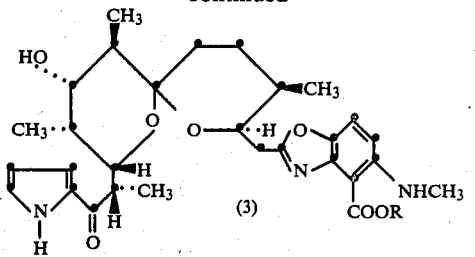

(3)

wherein R is methyl, ethyl, n-propyl, i-propyl, n-butyl, i-butyl, or t-butyl.

2. A compound of the formula:

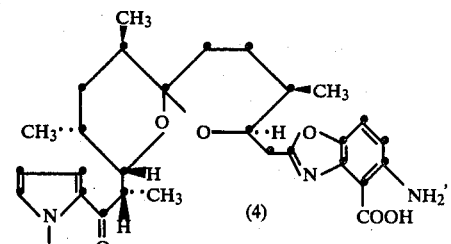

(4)

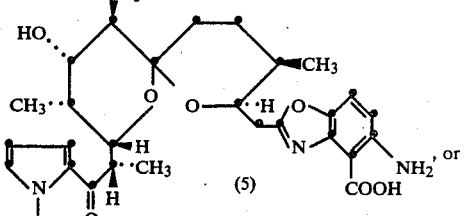

(5)

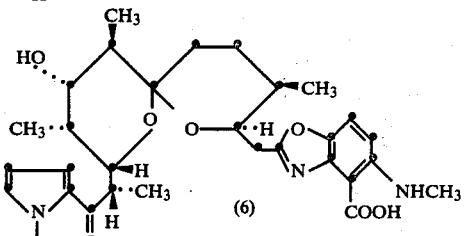

(6)

or a sodium, potassium, or lithium salt thereof; or a dimeric complex thereof with a divalent cation selected from the group consisting of berylium, magnesium, calcium, strontium, barium, manganese, cadmium, iron, zinc, lead, and mercury.

* * * * *